United States Patent
Hermelin et al.

(10) Patent No.: US 6,793,935 B2
(45) Date of Patent: Sep. 21, 2004

(54) MINERAL SUPPLEMENT

(75) Inventors: Marc S. Hermelin, Glendale, MO (US); George Paradissis, St. Louis, MO (US); James A. Garegnani, Ballwin, MO (US)

(73) Assignee: KV Pharmaceutical Company, St. Louis, MO (US)

( * ) Notice: Subject to any disclaimer, the term of this patent is extended or adjusted under 35 U.S.C. 154(b) by 37 days.

(21) Appl. No.: 10/080,390

(22) Filed: Feb. 25, 2002

(65) Prior Publication Data

US 2002/0119183 A1 Aug. 29, 2002

Related U.S. Application Data

(62) Division of application No. 09/583,890, filed on May 31, 2000, now abandoned.

(51) Int. Cl.$^7$ ................................................. A61K 9/26
(52) U.S. Cl. ...................... 424/469; 424/438; 424/442; 424/464; 424/679
(58) Field of Search ................................ 424/464–465, 424/468–470, 663, 679, 438–442

(56) References Cited

U.S. PATENT DOCUMENTS

| | | | |
|---|---|---|---|
| 4,259,315 A | | 3/1981 | Lippmann et al. |
| 4,265,874 A | | 5/1981 | Bonsen et al. |
| 4,764,375 A | * | 8/1988 | Paradissis .................... 424/153 |
| 4,863,743 A | * | 9/1989 | Hsiao et al. ................. 424/426 |
| 4,952,402 A | | 8/1990 | Sparks et al. |
| 4,983,404 A | | 1/1991 | Raman et al. |
| 4,990,341 A | | 2/1991 | Goldie et al. |
| 5,004,595 A | | 4/1991 | Cherukuri et al. |
| 5,051,263 A | | 9/1991 | Barry et al. |
| 5,084,287 A | | 1/1992 | Ghebre-Sellassie et al. |
| 5,211,957 A | | 5/1993 | Hagemann et al. |
| 5,399,357 A | | 3/1995 | Akiyama et al. |
| 5,567,439 A | * | 10/1996 | Myers et al. ................ 424/486 |
| 5,576,022 A | | 11/1996 | Yang et al. |
| 5,587,179 A | | 12/1996 | Gergely et al. |
| 5,662,933 A | | 9/1997 | Baichwal et al. |
| 5,670,170 A | | 9/1997 | Grimmett et al. |
| 5,686,094 A | | 11/1997 | Acharya |
| 5,695,784 A | | 12/1997 | Pöllinger et al. |
| 5,707,646 A | | 1/1998 | Yajima et al. |
| 5,824,339 A | | 10/1998 | Shimizu et al. |
| 5,858,412 A | | 1/1999 | Staniforth et al. |
| 5,888,930 A | | 3/1999 | Smith et al. |
| 5,891,474 A | | 4/1999 | Busetti et al. |
| 6,365,182 B1 | | 4/2002 | Khankari et al. ........... 424/466 |

OTHER PUBLICATIONS

*The Merck Manual*, 135–139 (17$^{th}$ ed. 1999).
*Physician's Desk Reference for Nonprescription Drugs*, 819–20 (20$^{th}$ Ed. 1999).
*Physician's Desk Reference for Nonprescription Drugs*, 827 (20$^{th}$ Ed. 1999).
*Physician's Desk Reference for Nonprescription Drugs*, 849–50 (20$^{th}$ Ed. 1999).
Recharge™ Sports Drink, R.K. Knudson advertisement.
Ferraz et al., *Revisita Brasileira de Ciencias Farmaceuticas*, 1999, 35(1), 95–99. 1999: 760273 HCAPLUS.
Li et al. *Drug Dev. Ind. Pharm.* (1991), 17(1), 27–37. HCAPLUS 1991:108860.
Li et al. *Drug Dev. Ind. Pharm.* (1991), 18(3), 333–43. HCAPLUS 1992:136170.
Suess, W., *Pharmazie* (1983), 38(7), 476–8. HCAPLUS 1983:581405.

* cited by examiner

Primary Examiner—Neil S. Levy
(74) Attorney, Agent, or Firm—Gary M. Nath

(57) ABSTRACT

The present invention is directed to a novel flavored extended release composition which forms a non-effervescent suspension when dropped into a liquid, and the methods of using said supplement, thereby minimizing and eliminating gastric discomfort. This flavored extended release composition provides the additional benefits of palatable taste and pleasant appearance.

26 Claims, No Drawings

MINERAL SUPPLEMENT

This application is a divisional application of U.S. patent application Ser. No. 09/583,890, filed May 31, 2000, now entire contents of which is hereby incorporated by reference in its entirety.

BACKGROUND OF THE INVENTION

1. Field of the Invention

The present invention is directed to a novel flavored extended release composition which forms a non-effervescent suspension when dropped into a liquid, and the methods of using said supplement, thereby improving swallowing through dispersing a large mass in a liquid and minimizing and eliminating gastric discomfort. This flavored extended release composition provides the additional benefits of palatable taste and pleasant appearance when dispersed into a liquid.

2. Description of the Related Art

Patients often encounter difficulty in complying with their drug regimen for various reasons. For example, dosage forms are often too large to comfortably swallow. In addition, many dosage forms taste unpalatable and even cause gastric discomfort. Further, patients have to take many doses throughout the day in order to maintain an effective blood level without taking toxic amounts.

An extended release dosage form remedies this problem because it can deliver the same amount of biologically active substance in one dose that an immediate release dosage form delivers in many doses. An extended release composition is one that achieves slow release of a biologically active substance over an extended period of time and extends the duration of action over that achieved by conventional delivery. An extended release drug delivery system provides several advantages over an immediate release drug delivery system of the same ingredient. These benefits include reduction of the frequency of administration and the maintenance of effective concentrations of the biologically active substance in the blood. The maintenance of an effective concentration in the blood reduces the chance of side effects and toxicity of the biologically active substance. This benefit is especially important when a toxic amount of a biologically active substance can cause illness and death.

Numerous approaches for administering extended and controlled release formulations have also been described in various references. For example, Busetti et al., U.S. Pat. No. 5,891,474, disclose a method of achieving a time specific delivery of a pharmaceutically active agent to a patient. The pharmaceutical agent is encased in a swellable polymeric coating, which delays the release of the pharmaceutical agent for a predetermined period of time depending on the thickness of the polymeric coating.

Baichwal et al., U.S. Pat. No. 5,662,933, disclose a extended release pharmaceutical formulation. The extended release formulation includes a gelling agent, an inert pharmaceutical diluent, a hydrophobic material and/or coating and a medicament for extended oral administration.

Goldie et al., U.S. Pat. No. 4,990,341, disclose a solid, controlled release oral dosage form. The dosage form comprises a therapeutic amount of hydromorphone or salt in a matrix for use with moderate to severe pain. The dosage is formulated such that the peak plasma level of hydromorphone is attained at 2–4 hours following administration of the dosage form.

Acharya, U.S. Pat. No. 5,686,094, discloses a controlled release formulation for the treatment of xerostomia. The delivery system comprises a polycarbophil coating surrounding an active agent. The coating system may also be used with cosmetics and household items where a controlled release effect is beneficial.

Yang et al., U.S. Pat. No. 5,576,022, disclose a controlled release tacrine drug delivery system comprising a sustained release composition and a controlled release composition wherein the controlled release composition is present at specific ratios to the immediate release composition.

Barry et al., U.S. Pat. No. 5,051,263, disclose a controlled release formulation comprising granules containing a carbomer and enough of an active substance to form a dose of the active substance. The granules are coated with an acrylic polymer. The solubility of the acrylic polymer controls the rate of dosage.

Sparks et al., U.S. Pat. No. 4,952,402, disclose a controlled release powder containing microparticles. The microparticles, which can contain an active pharmaceutical, have a predetermined dissolution rate which controls the rate of dosage. The powder is useful in foods and pharmaceuticals.

Staniforth et al., U.S. Pat. No. 5,858,412, disclose a sustained release formulation comprising augmented microcrystalline cellulose, and active ingredient and a sustained release carrier. The sustained release dosage form may be a tablet or a capsule containing excipients appropriate for sustained release technology.

Akiyama et al., U.S. Pat. No. 5,399,357, disclose a matrix prepared by dispersing a pharmaceutical active into a matrix comprised of either a fatty acid ester or a polyglycerol. The preparation has stable release controlling abilities, which contribute to the reduction of administration time of the active as well as a reduction of side effects.

Smith et al., U.S. Pat. No. 5,888,930, disclose a controlled release spray comprising a polymeric microporous bead containing an active ingredient. The bead has an anisotropic pore structure of large pores in the interior and small pores at the surface, with the graduation of pore size being continuous. The controlled diffusion of the active ingredient results in a controlled release product that reduces side effects and has a high stability.

Gergely et al., U.S. Pat. No. 5,587,179, disclose a pharmaceutical formulation in the form of an effervescent and/or disintegrating tablet. The biologically active substance, having an irritating taste, is coated by a matrix. This mixture may additionally contain a composition to compensate for electrolyte and salt loss in the body. Barry et al., U.S. Pat. No. 5,051,263, disclose a controlled release formulation comprising granules containing a carbomer and enough of an active substance to form a dose of the active substance. The granules are coated with an acrylic polymer. The solubility of the acrylic polymer controls the rate of dosage.

Sparks et al., U.S. Pat. No. 4,952,402, disclose a controlled release powder containing microparticles. The microparticles, which can contain an active pharmaceutical, have a predetermined dissolution rate which controls the rate of dosage. The powder is useful in foods and pharmaceuticals.

Staniforth et al., U.S. Pat. No. 5,858,412, disclose a sustained release formulation comprising augmented microcrystalline cellulose, an active ingredient and a sustained release carrier. The sustained release dosage form may be a tablet or a capsule containing excipients appropriate for sustained release technology.

Akiyama et al., U.S. Pat. No. 5,399,357, disclose a matrix prepared by dispersing a pharmaceutical active into a matrix comprised of either a fatty acid ester or a polyglycerol. The preparation has stable release controlling abilities, which contribute to the reduction of administration time of the active as well as a reduction of side effects.

Smith et al., U.S. Pat. No. 5,888,930, disclose a controlled release spray comprising a polymeric microporous bead containing an active ingredient. The bead has an anisotropic pore structure of large pores in the interior and small pores at the surface, with the graduation of pore size being continuous. The controlled diffusion of the active ingredient results in a controlled release product that reduces side effects and has a high stability.

Gergely et al., U.S. Pat. No. 5,587,179, disclose a pharmaceutical formulation in the form of an effervescent and/or disintegrating tablet. The active ingredient, having an irritating taste, is coated by a matrix. This mixture may additionally contain a composition to compensate for electrolyte and salt loss in the body.

Pöllinger et al, U.S. Pat. No. 5,695,784, disclose a flavor-masked pharmaceutical preparation. The preparation allows the administration of pharmaceutically active substances having a very unpleasant organoleptic taste, even in liquid form.

Cherukuri et al., U.S. Pat. No. 5,004,595, disclose a free-flowing particulate delivery system for providing enhanced flavor and sweetness to comestible compositions. The system comprises a powdered flavor composition encapsulated in a matrix comprised of a hydrophilic coating. The system is especially useful in pharmaceutical preparations as well as chewing gum.

Myers et al., U.S. Pat. No. 5,567,439, disclose a method and dosage unit form for delivery of a controlled release system. The controlled release system comprises instantaneous release components and delayed release components and is mixed with an uncured shearform matrix.

Ghebre-Sellassie et al., U.S. Pat. No. 5,084,287, disclose a pharmaceutical preparation comprising drug micropellets surrounded by a controlled release coating.

Yajima et al., U.S. Pat. No. 5,707,646, disclose the method of dissolving a drug in a polymer compound in a basic oxide containing sugar alcohol. This oral preparation is useful in masking the unpleasant taste of most drugs.

Raman et al., U.S. Pat. No. 4,983,404, disclose a flavor delivery system which offers a combination of extended and increased flavor intensity in chewing gum. The system is also useful in pharmaceuticals and food products as well as scratch-and-sniff packaging.

Regardless of the extended release properties of a dosage form, patients often find it difficult to comply with their drug regimen because the dosage form is large and difficult to swallow. This problem may be avoided by suspending the biologically active substance in a liquid that the patient can drink. However, patients may still have difficulty drinking the suspension if it is effervescent. Non-effervescent suspensions are easier to ingest, especially if the patient is nauseous.

Numerous approaches for administering an biologically active substance in an effervescent liquid suspension have been described in various references. For example, Hagemann et al., U.S. Pat. No. 5,211,957, disclose a solid, rapidly disintegrating effervescent tablet which produces an aqueous suspension when placed in liquid. The liquid dosage form contains diclofenac in micronised form provided with a swellable coating.

Grimmett et al., U.S. Pat. No. 5,670,170, disclose a pharmaceutical formulation comprising a medicament coupled with an effervescent component. The formulation may be suspended in water and imbibed. The preferred medicaments are antibiotics in combination with a citric acid-sodium bicarbonate couple.

Shimizu et al., U.S. Pat. No. 5,824,339, disclose an effervescent composition comprising a powder containing acid sensitive drugs that may be suspended in solution. The suspension provides a refreshing sensation upon ingestion.

Bonsen, U.S. Pat. No. 4,265,874, discloses a method for delivering a drug in a liquid. The drug provides an effervescent suspension in an environment that delivers the drug. The effervescence would cause the drug to have limited solubility under neutral and acid conditions.

In addition, approaches for administering a biologically active substance in a non-effervescent liquid suspension have also been described. For example, Recharge™ Sports Drink, made by R. K. Knudson, Inc., is a fruit flavored drink designed for use during active sports to replace sodium and potassium lost during vigorous exercise. The drink contains 50 mg of potassium electrolyte. See R. K. Knudson advertisement.

The specific drug delivery system which is used to deliver a biologically active substance will have a great impact on the efficacy of that substance. For example, a variety of drug delivery systems have been utilized to effectively provide appropriate amounts of electrolytes. Electrolytes are essential to the body to regulate fluid balance. Electrolytes are salts that dissolve in water and dissociate. Cells cannot hold on to water molecules directly, but the polar nature of water causes it to aggregate around charged ions. See The Merck Manual, 135 (17$^{th}$ Ed. 1999). Cells sort out mineral ions so that some reside primarily outside the cell (for example, sodium and chloride) or primarily inside (for example, potassium and sulfate). During nerve transmission and muscle contraction, potassium and sodium change places across the cell membrane. The cell then quickly pumps them back into place. See Id. The relationship between intracellular and extracellular potassium concentrations strongly influences cell membrane polarization, which in turn influences important cell processes, such as the conduction of nerve impulses and muscle cell contraction. See Id. at 136.

The amount of various salts in the body must remain constant. If salts are lost, they must be replaced from an external source. Some situations, such as excessive vomiting, diarrhea, sweating, burns and the like may result in so much salt loss from that body that a medical emergency could result. See Id.

The electrolyte potassium plays an essential role in maintaining fluid and electrolyte balance as well as cell integrity through its role in the sodium-potassium pump. Small alterations in plasma potassium concentrations can have major clinical manifestations. Therefore, the control of extracellular potassium concentration is a very high priority for the body. See Id. at 137.

Numerous factors affect the movement of potassium between the intracellular and extracellular fluid compartments. The most important factor is circulating insulin level. In the presence of insulin, potassium moves into cells. When circulating insulin is lacking, as with diabetes, potassium moves out of cells, raising the potassium plasma concentration. Stimulation of the sympathetic nervous system also affects transcellular movement. Beta-agonists promote the cellular uptake of potassium, while beta-blockers promote movement of potassium out of cells. Plasma pH also affects potassium concentrations. Acute metabolic acidosis promotes the movement of potassium out of cells. Changes in plasma $HCO_3$ has the same effect. See Id. at 138.

There are several disorders of potassium metabolism, including hypokalemia, an abnormal movement of potassium into the cells, and hyperkalemia, an abnormal movement of potassium out of the cells. See Id. at 135–36 (17th Ed. 1999).

Because some potassium is found inside all living cells, most plants and animals can be a source of potassium. The best source for potassium is fresh fruits, vegetables and legumes. Accordingly, dietary deficiency of potassium is possible on a diet low on fruits and vegetables, although potassium deficiency occurs most commonly due to excessive losses of fluids. Conditions such as diabetic acidosis, dehydration, pica, villenous adenoma of the colon, prolonged vomiting or diarrhea can cause potassium deficiency. The regular use of certain drugs such a diuretics, steroids and laxatives also result in potassium deficiency. The first symptom of potassium deficiency is muscle weakness, followed by confusion and paralysis. See Id. at 137–38.

Potassium toxicity will not often result if the only source of potassium is food. However, toxicity may result from the overuse of potassium salt, especially in infants and the elderly. When the body receives too much potassium, the kidneys speed up the rate of excretion and eventually wear out. If the GI tract is bypassed, the excess potassium results in immediate death. If potassium is injected directly into a vein, the heart stops. See Id at 137.

Potassium chloride is the most common treatment for hypokalemia and hyperkalemia. However, potassium chloride is a known irritant to the gastrointestinal tract, and administration of the salt can cause nausea, vomiting, epigastric distress, abdominal discomfort and diarrhea. Excessive doses can cause weakness, listlessness, mental confusion, hypotension, vertigo, heart block and even death. Potassium chloride often shows signs of toxicity when administered to humans and should be administered carefully. See Id. at 139.

Various dosage forms of potassium chloride, such as uncoated and enteric-coated tablets and microcapsules have been used in the administration to humans, but frequently cause gastrointestinal ulcers, obstruction, hemorrhage and perforation as well as the symptoms of toxicity mentioned above. Various approaches for administering potassium have been described in published literature and various references. For example, Lippmann et al., U.S. Pat. No. 4,259,315, disclose pharmaceutical compositions for treating potassium deficiency in monogastric animals comprising controlled release gelatin capsules containing potassium salt and hydrophillic surfactant. The potassium chloride is contained in controlled release microcapsules and the surfactant reduces the likelihood of damage to mucosa.

Hsaio et al., U.S. Pat. No. 4,863,743, disclose a controlled release potassium chloride tablet comprising potassium chloride crystals coated with ethylcellulose and hydroxypropylcellulose. The coated crystals form micro pellets that can be crushed into tablets. These tablets disintegrate in an aqueous environment assuring a uniform dissolution of the active ingredient, which ensures a wide distribution of potassium over the gastric mucosa.

Mineral supplements containing potassium have also been described in various references. The Physician's Desk Reference for Nonprescription Drugs describes various vitamin and mineral supplements which contain potassium. For example, One-A-Day® Maximum Multivitamin/Multimineral Supplement, made by Bayer Corporation, is a multivitamin and mineral supplement indicated as a dietary supplement to be administered once a day. The supplement contains 80 mg of potassium, 2% of the recommended daily allowance. See *Physician's Desk Reference for Nonprescription Drugs,* 827 (20th Ed. 1999).

Macro-Mineral Complex, made by AdvoCare International, is a mineral supplement incorporating the full spectrum of bone-building nutrients in a bioavailable form to be taken two to six times a day. Each dosage contains 250 mg of potassium bicarbonate. See *Physician's Desk Reference for Nonprescription Drugs,* 819 (20th Ed. 1999).

Vitasana™ Daily Dietary Supplement, made by Pharmaton Natural Health Products, is a ginseng and multivitamin/mutimineral combination indicated as a dietary supplement for health and vitality, and is administered in gelcap form. This supplement should be taken twice a day and contains 16 mg of potassium chloride. See *Physician's Desk Reference for Nonprescription Drugs,* 850 (20th Ed. 1999).

While electrolytes are vital to maintaining fluid balance and cell integrity, most sources of electrolytes present problems with patient compliance. For example, most compositions containing electrolytes are large and difficult to swallow. Alternatively, liquid dosage forms are easy to administer. Patients experiencing nausea and vomiting require electrolytes to replenish lost body fluids, however a patient experiencing nausea has great difficulty swallowing large tablets, as well as effervescent liquid suspensions. Alternatively, non-effervescent liquid suspensions are easy to administer. Furthermore, electrolyte supplements have an unpleasant taste that make the supplement ever more unpalatable, especially to children and the elderly. The above described compositions fail to fulfill the need for a non-effervescent tablet containing electrolytes which may be administered in liquid form.

In addition, the electrolyte potassium chloride is a known gastric irritant. Solid forms of potassium chloride lay along the stomach or intestinal lining and ulcerate the stomach or intestinal wall, leading to internal bleeding. Potassium chloride supplements that are not evenly dispersed and undiluted can cause great gastric discomfort and pain, if not injury.

Therefore, it would be desirable to provide a composition in an extended release form which overcomes the difficulties experienced in oral administration of large tablets and which would also have a palatable taste, while providing an appropriate dosage of an active which would be diluted and evenly dispersed before digestion. Such a supplement would be easier to administer, thereby increasing patient compliance. It would also be desirable to provide a drug delivery system which overcomes the side effects typically associated with the administration of certain substances, such as potassium, as well as to provide a solid dosage form of the above which would allow for ease of storage and transportation, and would not become suspended until the solid dosage form is placed in liquid. Accordingly, it would be desirable to provide a flavored and/or colored extended release composition which overcomes the deficiencies of the currently available compositions.

SUMMARY OF THE INVENTION

The present inventive subject matter provides a flavored extended release composition which forms a non-effervescent suspension when dropped into a liquid, and the methods of using said supplement. The present compositions overcome the deficiencies of current extended release compositions by minimizing and eliminating gastric discomfort, as well as providing the additional benefits of palatable taste and pleasant appearance.

One embodiment of the present inventive subject matter is a composition for oral administration to an animal, which comprises a plurality of extended release particles containing a biologically active substance, said particles being formulated in a solid dispersible tablet; a flavoring agent being formulated in the solid dispersible tablet; wherein the solid dispersible tablet forms a non-effervescent flavored and/or colored suspension when placed in a liquid; and wherein the non-effervescent flavored suspension after being orally administered to the animal releases the biologically active substance over a period of about 2 hours to about 48 hours.

A further embodiment of the present inventive subject matter is a composition for oral administration to an animal, which comprises a plurality of extended release particles containing a biologically active substance; a flavoring agent being formulated in the extended release particles; wherein the plurality of extended release particles forms a non-effervescent flavored suspension when placed in a liquid; and wherein the non-effervescent flavored suspension after being orally administered to the animal releases the biologically active substance over a period of about 2 hours to about 48 hours.

Another embodiment of the present inventive subject matter is a composition for oral administration to an animal, which comprises a plurality of extended release particles containing an alkaline salt of potassium, said particles being formulated in a solid dispersible tablet; a flavoring agent being formulated in the solid dispersible tablet; wherein the solid dispersible tablet forms a non-effervescent flavored and/or colored suspension when placed in a liquid; and wherein the non-effervescent flavored suspension after being orally administered to the animal releases the alkaline salt of potassium over a period of about 2 hours to about 48 hours.

Yet another embodiment of the present inventive subject matter is a method of improving patient compliance with a therapeutic or nutritional regimen, which comprises administering to an animal a non-effervescent flavored suspension formed by placing into a liquid a solid dispersible tablet comprising a flavoring and/or coloring agent and a plurality of particles containing a biologically active substance, said particles being coated with an extended release coating agent; wherein the non-effervescent flavored suspension after being orally administered to the animal releases the biologically active substance over a period of about 2 hours to about 48 hours.

An even further embodiment of the present inventive subject matter is a method of preparing an extended release composition for oral administration to an animal, which comprises coating a plurality of particles of a biologically active substance with an extended release coating agent to form extended release particles; blending the extended release particles, a flavoring agent and at least one excipient to form a compressible mixture; and compressing the compressible mixture into solid dispersible tablets which form a non-effervescent flavored and/or colored suspension when placed into a liquid.

The present inventive subject matter also included a method of preparing a potassium chloride composition for oral administration to an animal, which comprises coating a plurality of potassium chloride crystals with a coating agent to form extended release potassium chloride particles; and blending the extended release potassium chloride particles with a flavoring and/or coloring agent and at least one excipient to form extended release potassium chloride particles which form a non-effervescent flavored and/or colored suspension when placed into a liquid.

DETAILED DESCRIPTION OF THE INVENTION

As used herein, "animal" refers to a human, mammal or any other animal.

"Biologically active substance" refers to any substance or substances comprising a drug, active therapeutic substance, metabolite, medicament, vitamin, or mineral, any substance used for treatment, prevention, diagnosis, cure or mitigation of disease or illness, any substance which affects anatomical structure or physiological function, or any substance which alters the impact of external influences on an animal, or metabolite thereof, and as used herein encompasses the terms "active substance", "therapeutic substance", "agent", "active agent", "drug", "medication", "medicine", "medicant", and other such similar terms.

"Form" refers to one discrete unit containing a designated amount of a composition.

"Solid disbursible tablet" is any solid which disperses in a liquid when placed in the liquid and allowed to dissolve or when stirred, mixed or blended until it is dissolved.

The present inventive subject matter provides a flavored extended release composition for oral administration to an animal, as well as methods of using same. The animal may be human. Furthermore, the human may be an adult. Alternatively, the human may be a child. The composition contains a plurality of extended release particles or granules containing an biologically active substance, and the particles or granules along with a flavoring agent are dispersed throughout a solid dispersible tablet. The tablet forms a non-effervescent, flavored suspension when placed in a liquid. Following oral administration to the animal, the flavored and/or colored suspension releases the biologically active substance over a period of about 2 hours to about 48 hours.

The present inventive subject matter also includes compositions for oral administration to an animal containing an alkaline salt of potassium. The present compositions comprise a plurality of extended release particles containing an alkaline salt of potassium, said particles being formulated in a solid dispersible tablet and a flavoring agent being formulated in the solid dispersible tablet. The solid dispersible tablet forms a non-effervescent flavored and/or colored suspension when placed into a liquid. After being orally administered to the animal, the non-effervescent flavored suspension releases the alkaline salt of potassium over a period of about 2 hours to about 48 hours.

The biologically active substance may be selected from the group consisting of analgesics, anti-inflammatories, antihistamines, antitussives, expectorants, decongestants, narcotics, bronchodilators, cardiovasculars, central nervous system drugs, anti-hypertensive agents, osteoporotic agents, GERD agents, anti-neoplastic agents, anti-asthmatics, hormone replacement agents, anti-infectives, anti-diabetics, lipid lowering agents, thrombolytic agents, anticoagulant agents, fibrinolytic agents, nutritional agents, vitamins, minerals, metal salts, electrolytes, herbal agents, fatty acids and mixtures thereof.

Preferably, at least one biologically active substance is an electrolyte. The electrolyte may be selected from the group consisting of sodium, potassium, calcium, magnesium, chloride, bicarbonate, phosphate, sulfate, organic acids and proteins. More preferably, the biologically active substance is an alkaline salt of potassium. The alkaline salt of potassium is preferably, but not limited to, potassium chloride.

The potassium chloride may be present in the supplement in an amount ranging from about 500 mg to about 2,500 mg.

Preferably, the potassium chloride may be present in the solid disintegratable tablet in an amount ranging from about 20% to about 98% and more preferably from about 65% to about 85%. Most preferably, the potassium chloride may be present in the solid disintegratable tablet in an amount ranging from about 70% to about 80%. The solid disintegratable tablet may release an amount of alkaline salt of potassium ranging from about 1 mEq to about 50 mEq, and preferably about 5 mEq to about 40 mEq.

It is of significant advantage to both the clinician and the patient that the supplement be formulated so that it may be administered in a minimum number of daily doses from which the drug is uniformly released over a desired, extended period of time. Often, the effectiveness of pharmaceuticals has a maximum life of a few hours in the body. As a result, the amount of active substance in the body fluctuates as the patient administers the composition every few hours, rather than remaining constant. Extended release dosage forms have delayed effects because of certain pharmaceutical excipients in the dosage form or because of the natural half-life of the biologically active substance in the body. An extended release dosage form can have a delayed effect ranging from 1 hour to 1 week. By administering the active substance in an extended release form, patients do not need to purchase and administer as many doses, which will result in higher patient compliance. Further, by administering exactly the desired amount of active substance, nothing is wasted, and the composition is cost effective.

The extended release particles or granules may comprise a compressible binding agent. The binding agent may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders well known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch and silicon dioxide. Preferably, the compressible binding agent is microcrystalline cellulose.

The extended release particles or granules may further comprise a coating agent. Non-limiting exemplary coating agents include hydroxypropyl methylcellulose, polyethylene glycol and mixtures thereof. Preferably, the hydroxypropyl methylcellulose can be present in the solid disintegratable tablet in an amount ranging from about 0.1% to about 25% by weight based on the total weight of the tablet. More preferably, the hydroxypropyl methylcellulose can be present in the solid disintegratable tablet in an amount ranging from about 0.5% to about 15% by weight based on the total weight of the tablet. Even more preferably, the hydroxypropyl methylcellulose can be present in the solid disintegratable tablet in an amount ranging from about 0.6% to about 10% by weight based on the total weight of the tablet. Preferably, the polyethylene glycol can be present in the solid disintegratable tablet in an amount ranging from about 0.01% to about 1.0% by weight based on the total weight of the tablet. More preferably, the polyethylene glycol can be present in the solid disintegratable tablet in an amount ranging from about 0.01% to about 0.40% by weight based on the total weight of the tablet.

Preferably, for a 6-hour period of administration, the extended release particles or granules may provide an in vitro dissolution rate, when measured at about 100 rpm in about 900 ml of an aqueous buffer having a pH between about 1.6 and about 7.2 and at a temperature of about 37 degrees Celsius, between about 5% and about 40% (by weight) of potassium salt released after about 1 hour, between about 20% and about 60% (by weight) of potassium salt released after about 2 hours, between about 45% and about 85% (by weight) potassium salt released after about 4 hours, and not less than 70% (by weight) potassium salt released after about 6 hours.

Preferably, for a 12-hour period of administration, the extended release particles or granules may provide an in vitro dissolution rate, when measured at about 100 rpm in about 900 ml of an aqueous buffer having a pH between about 1.6 and about 7.2 and at a temperature of about 37 degrees Celsius, between about 5% and about 50% (by weight) of potassium salt released after about 1 hour, between about 10% and about 75% (by weight) potassium salt released after about 2 hours, between about 20% and about 90% (by weight) potassium salt released after about 4 hours, NLT 50% (by weight) potassium salt released after about 6 hours, and NLT 60% (by weight) potassium salt released after about 9 hours.

Preferably, for a 24-hour period of administration, the extended release particles or granules may provide an in vitro dissolution rate, when measured at about 100 rpm in about 900 ml of an aqueous buffer having a pH between about 1.6 and about 7.2 and at a temperature of about 37 degrees Celsius, between about 5% and about 50% (by weight) of potassium salt released after about 1 hour, between about 20% and about 60% (by weight) of potassium salt released after about 6 hours, between about 30% and about 70% (by weight) potassium salt released after about 12 hours, between about 40% and about 80% (by weight) potassium salt released after about 18 hours, and not less than 60% (by weight) potassium salt released after about 24 hours.

More preferably, the extended release particles or granules may provide an in vitro dissolution rate, when measured at about 100 rpm in about 900 ml of an aqueous buffer having a pH between about 1.6 and about 7.2 and at a temperature of about 37 degrees Celsius, between about 5% and about 40% (by weight) of potassium salt released after about 1 hour, between about 20% and about 60% (by weight) potassium salt released after about 2 hours, between about 45% and about 85% (by weight) potassium salt released after about 4 hours, NLT 70% (by weight) potassium salt released after about 6 hours, and between about 15% to about 35% (by weight) potassium salt released after about 9 hours.

Even more preferably, the extended release particles or granules may provide an in vitro dissolution rate, when measured at about 100 rpm in about 900 ml of an aqueous buffer having a pH between about 1.6 and about 7.2 and at a temperature of about 37 degrees Celsius, between about 20% and about 25% (by weight) of potassium salt released after about 1 hour, between about 20% and about 25% (by weight) potassium salt released after about 2 hours, between about 20% and about 25% (by weight) potassium salt released after about 4 hours, between about 20% and about 25% (by weight) potassium salt released after about 6 hours, and between about 20% to about 25% (by weight) potassium salt released after about 9 hours.

After a single oral 4-tablet dose, equivalent to 80 mEq of potassium, the extended release particles or granules may provide a mean maximum urinary excretion rate of potassium from about 7 mEq/hr to about 9 mEq/hr from a mean of about 4 to about 6 hours after administration, a mean amount of potassium excreted in the urine over a 24-hour period of about 70 mEq to about 80 mEq, and a mean amount of potassium excreted in the urine over a 48-hour period of about 115 mEq to about 130 mEq.

The extended release particles may be pH-sensitive. Preferably, the extended release particles may dissolve in fluids having a pH of less than about 4. More preferably, the extended release particles may dissolve in fluids having a pH of less than about 2. The liquid may have a pH ranging from about 2 to 14. More preferably, liquid may have a pH ranging from about 4 to 14.

The extended release particles or granules may contain a polyacrylate dispension in an amount ranging from about 5% to about 30% by weight of the total weight of the solid disintegrable tablet.

Preferably, the extended release particles may have a mesh size ranging from about 10 to about 100 mesh. More preferably, the extended release particles may have a mesh size ranging from about 12 to about 80 mesh. Even more preferably, the extended release particles may have a mesh size ranging from about 12 to about 40 mesh.

The non-effervescent flavored suspension can be a uniform suspension. Preferably, the non-effervescent flavored suspension may have a viscosity ranging from about 5 cp to about 100 cp. More preferably, the non-effervescent flavored suspension may have a viscosity ranging from about 25 cp to about 75 cp. Even more preferably, the non-effervescent flavored suspension may have a viscosity ranging from about 40 cp to about 50 cp.

Drinking a composition suspended in a liquid is often easier and more pleasant for most patients than swallowing a pill. Because of the absence of carbonation, non-effervescent suspensions are easier to ingest than effervescent suspensions, especially if the patient is either experiencing nausea or is predisposed to nausea.

Preferably, the non-effervescent flavored suspension may be formed in less than about 10 minutes after the solid dispersible tablet is placed in the liquid. More preferably, the non-effervescent flavored and/or colored suspension may be formed in less than about 5 minutes after the solid dispersible tablet is placed in the liquid. Even more preferably, the non-effervescent flavored and/or colored suspension may be formed in less than about 1 minute after the solid dispersible tablet is placed in the liquid. Even more preferably, the non-effervescent flavored and/or colored suspension may be formed in less than about 30 seconds after the solid dispersible tablet is placed in the liquid.

The solid dispersible tablet may be a self-dispersing tablet. The solid dispersible tablet may contain a disintegrant or a lubricant to assist in dispersing the active components until they dissolve.

The non-effervescent flavored suspension may be formed upon stirring, mixing or blending the liquid after the solid dispersible tablet is placed in said liquid. The non-effervescent flavored suspension may also be formed without stirring, mixing or blending the liquid after the solid dispersible tablet is placed in said liquid.

The non-effervescent flavored suspension will provide improved patient compliance with potassium supplementation. Because most potassium supplements are large and difficult to swallow, taste bad and often cause gastric discomfort, many patients do not like to administer potassium supplements. Accordingly, patient compliance with potassium supplements is low. Because the present inventive subject matter is a oral dosage form suspended in liquid, patients do not have to try to swallow a large pill. The non-effervescent nature of the resulting suspension also assists in the ease of swallowing. Further, because of the presence of a flavoring and/or coloring agent, the present inventive subject matter has a palatable taste. Furthermore, because the present inventive subject matter is dispersed evenly throughout the liquid when it disintegrates, gastric discomfort associated with concentrated potassium chloride dosages are reduced or eliminated.

Exemplary non-limiting liquids, in which the tablet is suspended, are water, milk, juices or mixtures and combinations thereof. The liquid is preferably water.

The solid disintegratable tablet can contain a natural or artificial sweetening agent. Accordingly, the non-effervescent flavored suspension has a pleasing taste when administered to an animal. The sweetening agent may also be selected from a wide range of materials such as water-soluble sweetening agents, water-soluble artificial sweeteners, and dipeptide based sweeteners, including salts thereof and mixtures thereof, without limitation. Preferably, but not limiting, the sweeting agent is aspartame.

Water-soluble sweetening agents are preferably monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol and mixtures thereof.

Water-soluble artificial sweetening agents are preferably saccharin salts such as sodium or calcium, saccharin salts, cyclamate salts, acesulfam-K and the like, and the free acid form of saccharin and mixtures thereof.

Dipeptide based sweetening agents are preferably L-aspartyl L-phenylalanine methyl ester.

Flavors which may optionally be added to the present compositions are those well known in the pharmaceutical art. For example, without limitation, synthetic flavor oils, and/or oils from plant leaves, flowers, fruits and so forth, and combinations thereof are useful. Non-limiting exemplary flavor oils include spearmint oil, peppermint oil, cinnamon oil, and oil of wintergreen (methylsalicylate). Also useful are artificial, natural or synthetic fruit flavors such as citrus oils including lemon, orange, grape, lime, and grapefruit, and fruit essences including apple, strawberry, cherry, pineapple and so forth, without limitation. Preferably, the flavor of the present composition is orange.

The solid disintegratable tablet can contain a coloring agent so that the resulting suspension is colored. Alternatively, the suspension may retain the color of the liquid. The color may be reflective of the specific flavoring agent employed or the color may be distinguishable from the flavoring agent in order to obtain a surprising patient response or effect.

The composition may be administered to improve patient compliance with taking the biologically active substance. Specifically, the composition may be administered to improve convenience of administration of the biologically active substance. The composition may be given as part of a multi-substance regimen. The color of the suspension may identify the biologically active substance to improve patient compliance with the multi-substance regimen.

Preferably, the composition, after being orally administered to an animal, may releases the biologically active substance over a period of about 4 hours to about 24 hours. More preferably, the composition, after being orally administered to an animal, may releases the biologically active substance over a period of about 12 hours to about 24 hours.

The dosage forms of the present invention may involve the administration of the composition in a single dose during a 24 hour period of time, a double dose during 24 hour period of time, or more than two doses during a 24 hour period of time, or fractional doses to be taken during a 24 hour period of time. The double or multiple doses may be taken simultaneously or at different times during the 24 hour period. Preferably, the composition may be administered once a day or twice a day.

The present composition may be divided into portions. When the composition is divided into portions, the portions may be even or uneven portions. One such portion may be administered during the morning or daytime and one may be administered in the evening or nighttime. For example, without being limited thereto, the potassium component of the composition could be divided so that one third of the total amount is administered in the morning or daytime and two thirds of the total amount are administered in the evening or nighttime.

The present inventive subject matter also includes methods of administering appropriate amounts of potassium. The present methods comprise administering to an animal a non-effervescent flavored and/or colored suspension by placing a solid disintegratable tablet into a liquid to form the suspension. The solid disintegratable tablet comprises a flavoring agent as well as a plurality of extended release particles or granules containing an alkaline salt of potassium.

Because tastemasking is a key feature of the present invention, use of the inventive liquid suspension as a solid system is contemplated, but not generally preferred. In such solid systems, the product would be taken orally and expected to be retained in the mouth for significant amounts of time to be solubilized and swallowed.

The present inventive subject matter also includes methods for improving patient compliance with a therapeutic or nutritional regimen. The present methods comprise administering to an animal a non-effervescent flavored suspension. The suspension is formed by placing into a liquid a solid dispersible tablet comprising a flavoring and/or coloring agent and a plurality of particles containing a biologically active substance. The particles are coated with an extended release coating agent. After being orally administered to the animal, the non-effervescent flavored suspension releases the biologically active substance over a period of about 2 hours to about 48 hours.

The present inventive subject matter also includes methods for preparing an extended release composition for oral administration to an animal. The present methods comprise coating a plurality of particles of a biologically active substance with an extended release coating agent to form extended release particles, blending the extended release particles, a flavoring agent and at least one excipient to form a compressible mixture and compressing the compressible mixture into solid dispersible tablets which form a non-effervescent flavored suspension when placed into a liquid.

The present inventive subject matter also includes methods for preparing an extended release composition containing potassium chloride for oral administration to an animal. The present methods comprise coating a plurality of potassium chloride crystals with a coating agent to form extended release potassium chloride particles and blending the extended release potassium chloride particles with a flavoring agent and at least one excipient to form extended release potassium chloride particles which form a non-effervescent flavored and/or colored suspension when placed into a liquid.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

EXAMPLES

Example I

Mineral Supplement

The following compositions were used to prepare the flavored extended release potassium chloride tablet of the present invention:

TABLE I

| Ingredient | Amount/tablet |
| --- | --- |
| Potassium Chloride ER granules | 20 mEq |
| Microcrystalline Cellulose | 220 mg |
| Orange Color | 20.0 |
| PEG | 2.0 |
| Orange Flavor | 170.0 |
| Sodium Stearyl Fumerate | 0.5 |
| Aspartame | 40.0 |

Nutritional supplements incorporating the above formulations were prepared using conventional methods and materials known in the pharmaceutical art in either controlled or immediate release forms. The resulting supplements were recovered and stored for future use.

Example II

Potassium Chloride Supplement

The following process and ingredients were used to prepare the potassium chloride extended release tablet of the present invention:

TABLE II

| Ingredient | Amount/tablet |
| --- | --- |
| Potassium Chloride ER Granule | 10 mEq |
| Calcium Phosphate Dibasic | 555.6 mg |
| Magnesium Oxide | 72.5 mg |
| Potassium Bicarbonate | 10 mg |
| Microcrystalline Cellulose | 218.6 mg |
| Orange flavor | 180 mg |
| Orange color | 20 mg |
| Sodium Stearyl Fumarate | 20.0 mg |
| Aspartame | 40.0 mg |
| Crospovidone | 40.0 mg |

All of the ingredients were blended using conventional methods. The resulting blend was compressed into tablets.

TABLE III

| Ingredient | Amount/tablet |
| --- | --- |
| Potassium Chloride ER Granule | 20 mEq |
| Ascorbic Acid | 33 mg |
| Microcrystalline Cellulose | 210 mg |
| Orange Flavor | 170.0 mg |
| Orange Color | 20.0 mg |
| Polyethylene Glycol | 2.0 mg |
| Sodium Stearyl Fumarate | 0.4 mg |
| Aspartame | 40.0 mg |

All the ingredients were blended using conventional methods. The resulting blend was compressed into tablets.

Example III

A flavored and/or colored extended release composition as set forth herein may be prepared in the following manner. The active components listed on Table II of Example II above are combined together with the excipients also listed on Table II. The resulting mixture is then blended together in a V-shaped blender and fed through the feed hopper of a Stokes BB2 tableting machine. A suitable number of tablets of the desired size may then be compressed.

Example IV

A patient is suffering from dehydration caused by prolonged vomiting. Because of the nausea, the patient has great difficulty swallowing a large, bitter pill. A flavored extended release composition containing electrolytes or a pharmaceutical composition comprising the same is administered. It would be expected that the patient would improve their condition or recover.

Example V

A patient is suffering from a potassium deficiency caused by chronic diabetic acidosis, but taking potassium supplements causes the patient gastric discomfort and too many supplements may lead to potassium toxicity. A mineral supplement in accordance with Example I is administered, eliminating the gastric discomfort and providing controlled release of potassium. It would be expected that the patient would improve their condition or recover.

Example VI

A panel of six patients are put on a dosage regimen, but each patient is given a different dosage form (ie. solid tablet, effervescent liquid suspensions and the non-effervescent liquid suspension of Example I). It would be expected that the highest patient compliance with the dosage regimen would be with the patient taking the non-effervescent liquid composition of Example I.

Example VII

A panel of six patients are given different dosage form (ie. solid tablet, effervescent liquid suspensions and the non-effervescent liquid suspension of Example I) to compare for taste. It would be expected that the best tasting dosage form would be the non-effervescent liquid composition of Example I.

The invention being thus described, it will be apparent that the same may be varied in many ways. Such variations are not to be regarded as a departure from the spirit and scope of the invention, and all such modifications are intended to be within the scope of the appended claims.

We claim:

1. A method of improving patient compliance with a therapeutic or nutritional regimen, which comprises:
    administering to an animal a non-effervescent flavored suspension formed by placing into a liquid a solid dispersible tastemasked tablet comprising a flavoring agent and a plurality of particles being coated with an extended release coating agent;
    wherein the solid dispersible tablet forms a non-effervescent flavored suspension when placed in a liquid having a viscosity of about 25 cp to about 75 cp; and
    wherein the non-effervescent flavored suspension after being orally administered to the animal releases the biologically active substance over a period of about 2 hours to about 48 hours.

2. The method of claim 1, wherein the non-effervescent flavored suspension is formed in less than about 10 minutes after the solid dispersible tablet is placed in the liquid.

3. The method of claim 1, wherein the non-effervescent flavored suspension is formed in less than about 5 minutes after the solid dispersible tablet is placed in the liquid.

4. The method of claim 1, wherein the non-effervescent flavored suspension is formed in less than about 1 minute after the solid dispersible tablet is placed in the liquid.

5. The method of claim 1, wherein the non-effervescent flavored suspension is formed in less than about 30 seconds after the solid dispersible tablet is placed in the liquid.

6. The method of claim 1, wherein the non-effervescent flavored suspension is formed upon stirring, mixing or blending the liquid after the solid dispersible tablet is placed in said liquid.

7. The method of claim 1, wherein the non-effervescent flavored suspension is formed without stirring, mixing or blending the liquid after the solid dispersible tablet is placed in said liquid.

8. The method of claim 1, wherein the solid dispersible tablet is a self-dispersing tablet.

9. The method of claim 1, wherein the non-effervescent flavored suspension after being orally administered to the animal releases the biologically active substance for a period of about 4 hours up to about 24 hours.

10. The method of claim 1, wherein the non-effervescent flavored suspension after being orally administered to the animal releases the biologically active substance for a period of about 12 hours up to about 24 hours.

11. The method of claim 1, wherein the solid dispersible tablet further contains a coloring agent, and wherein the suspension is a colored suspension.

12. The method of claim 1, wherein said non-effervescent flavored suspension is administered as part of a multi-substance. regimen.

13. The method of claim 12, wherein the color of the suspension identifies the biologically active substance to improve patient compliance with the multi-substance regimen.

14. The method of claim 1, wherein said non-effervescent flavored suspension is administered to improve patient compliance with taking the biologically active substance.

15. The method of claim 1, wherein the non-effervescent flavored suspension is administered to improve convenience of administration of the biologically active substance.

16. The method of claim 1, wherein the solid dispersible tablet further contains a natural or artificial sweetening agent.

17. The method of claim 1, wherein the biologically active substance is selected from the group consisting of analgesics, anti-inflammatories, antihistamines, antitussives, expectorants, decongestants, narcotics, bronchodilators, cardiovasculars, central nervous system drugs, anti-hypertensive agents, osteoporotic agents, GERD agents, anti-neoplastic agents, anti-asthmatics, hormone replacement agents, anti-infectives, anti-diabetics, lipid lowering agents, thrombolytic agents, anticoagulant agents, fibrinolytic agents, nutritional agents, vitamins, minerals, metal salts, electrolytes, herbal agents and fatty acids.

18. The method of claim 1, wherein the biologically active substance is an alkaline salt of potassium.

19. The method of claim 18, wherein the alkaline salt of potassium is potassium chloride.

20. The method of claim 1, wherein the liquid is water.

21. The method of claim wherein the non-effervescent flavored suspension has a pleasing taste when administered to the animal.

22. The method of claim 1, wherein the non-effervescent flavored suspension is administered once a day.

23. The method of claim wherein the non-effervescent flavored suspension is administered at least twice a day.

24. The method of claim 1, wherein the animal is a mammal.

25. A method of improving patient compliance with a therapeutic regimen, which comprises:
   administering to an animal a non-effervescent flavored suspension formed by placing into a liquid a solid dispersible tastemasked tablet comprising a flavoring agent and a plurality of particles being coated with an extended release coating agent;
   wherein the solid dispersible tablet forms a non-effervescent flavored suspension when placed in a liquid having a viscosity of about 25 cp to about 75 cp; and
   wherein the non-effervescent flavored suspension after being orally administered to the animal releases the biologically active substance over a period of about 2 hours to about 48 hours.

26. The method of claim 1, wherein the biologically active substance is a cardiovascular agent.

* * * * *

UNITED STATES PATENT AND TRADEMARK OFFICE
CERTIFICATE OF CORRECTION

PATENT NO. : 6,793,935 B2
DATED : September 21, 2004
INVENTOR(S) : Hermelin et al.

It is certified that error appears in the above-identified patent and that said Letters Patent is hereby corrected as shown below:

Column 16,
Line 52, replace "substance.regimen" with -- substance regimen --

Column 17,
Line 15, replace "claim wherein" with -- claim 1, wherein --

Signed and Sealed this

Thirty-first Day of May, 2005

JON W. DUDAS
*Director of the United States Patent and Trademark Office*